United States Patent
Roberts et al.

(10) Patent No.: US 9,962,346 B2
(45) Date of Patent: *May 8, 2018

(54) TREATMENT OF NAFLD AND NASH

(71) Applicant: CymaBay Therapeutics, Inc., Newark, CA (US)

(72) Inventors: Brian Roberts, Los Altos, CA (US); Xueyan Wang, Foster City, CA (US); Yun-Jung Choi, Fremont, CA (US); David Karpf, Mountain View, CA (US); Robert Martin, San Ramon, CA (US); Charles McWherter, Oakland, CA (US)

(73) Assignee: CymaBay Therapeutics, Inc., Newark, CA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/447,895

(22) Filed: Mar. 2, 2017

(65) Prior Publication Data

US 2018/0008566 A1    Jan. 11, 2018

Related U.S. Application Data

(63) Continuation of application No. 15/171,910, filed on Jun. 2, 2016, now Pat. No. 9,616,039, which is a continuation of application No. 14/684,100, filed on Apr. 10, 2015, now Pat. No. 9,381,181.

(60) Provisional application No. 61/978,335, filed on Apr. 11, 2014.

(51) Int. Cl.
*A61K 31/33* (2006.01)
*A61K 31/192* (2006.01)
*A61K 9/00* (2006.01)

(52) U.S. Cl.
CPC .......... *A61K 31/192* (2013.01); *A61K 9/0053* (2013.01); *A61K 31/33* (2013.01)

(58) Field of Classification Search
None
See application file for complete search history.

(56) References Cited

U.S. PATENT DOCUMENTS

| | | | |
|---|---|---|---|
| 5,712,279 A | 1/1998 | Biller et al. | |
| 5,739,135 A | 4/1998 | Biller et al. | |
| 5,883,109 A | 3/1999 | Gregg et al. | |
| 6,066,653 A | 5/2000 | Gregg et al. | |
| 6,166,197 A | 12/2000 | Cook et al. | |
| 6,222,025 B1 | 4/2001 | Cook et al. | |
| 6,451,991 B1 | 9/2002 | Martin et al. | |
| 7,015,315 B1 | 3/2006 | Cook et al. | |
| 7,101,993 B1 | 9/2006 | Cook et al. | |
| 7,301,050 B2 | 11/2007 | Kuo et al. | |
| 7,407,943 B2 | 8/2008 | Crooke et al. | |
| 7,511,131 B2 | 3/2009 | Crooke et al. | |
| 7,635,718 B2 | 12/2009 | Kuo et al. | |
| 7,932,268 B2 | 4/2011 | Rader | |
| 8,106,095 B2 | 1/2012 | Kuo et al. | |
| 2010/0152295 A1 | 6/2010 | Karpf et al. | |
| 2015/0139987 A1 | 5/2015 | Martin et al. | |
| 2015/0265560 A1 | 9/2015 | Boudes et al. | |
| 2015/0374649 A1 | 12/2015 | Boudes et al. | |

FOREIGN PATENT DOCUMENTS

| | | |
|---|---|---|
| WO | 2007/033231 A2 | 3/2007 |
| WO | 2012/154999 A1 | 11/2012 |

OTHER PUBLICATIONS

Amgen, Repatha Prescribing Information, revised Sep. 2015, URL: http://pi.amgen.com/united_states/repatha/repatha_pi_hcp_english.pdf.

Bays et al., "MBX-8025, A Novel Peroxisome Proliferator Receptor-δ Agonist: Lipid and Other Metabolic Effects in Dyslipidemic Overweight Patients Treated with and without Atorvastatin", J. Clin. Endocrin. Metab., 96(9), 2889-2897 (2011).

Belfort et al., "A placebo-controlled trial of pioglitazone in subjects with nonalcoholic steatohepatitis", N. Engl. J. Med., 355, 2297-2307 (2006).

Berglund et al., "Evaluation and Treatment of Hypertriglyceridemia: An Endocrine Society Clinical Practice Guideline", J. Clin. Endocrinol. Metab., 97(9), 2969-2989 (2012).

Beuers et al., "Changing nomenclature for PBC: from 'cirrhosis' to 'cholangitis'", Gut, 64(11), 1671-1672 (2015), published online in "Gut Online First" on Sep. 14, 2015 as 10.1136/gutjnl-2015-310593.

Choi et al., "Effects of the PPAR-δ agonist MBX-8025 on atherogenic dyslipidemia", Atherosclerosis, 220, 470-476 (2012).

clinicaltrials.gov, NCT02472535, "Study to Evaluate the Effects of MBX-8025 in Patients with HoFH", first received May 22, 2015, URL: https://clinicaltrials.gov/ct2/show/NCT02472535 [retrieved on Jun. 11, 2016].

clinicaltrials.gov, NCT02609048, "Study to Evaluate the Effects of Two Doses of MBX-8025 in Subjects With Primary Biliary Cirrhosis (PBC)", first received Nov. 13, 2015, URL: https://clinicaltrials.gov/ct2/show/NCT02609048 [retrieved on Jun. 11, 2016].

Cuchel et al., "Inhibition of Microsomal Triglyceride Transfer Protein in Familial Hypercholesterolemia", N. Engl. J. Med., 356(2), 148-156 (2007).

Cuchel et al., "Phase 3 study of microsomal triglyceride transfer protein inhibitor (MTP-I) lomitapide in subjects with homozygous familial hypercholesterolemia (HoFH)", Atherosclerosis Supp., 11(2), 14 (2010), Abstract L5.

Cymabay, "CymaBay Therapeutics Announces Preclinical Data Demonstrating the Potential of MBX-8025 to Treat Homozygous Familial Hypercholesterolemia", Jan. 28, 2015, URL: http://content.equisolve.net/cymabay/news/2015-01-28_CymaBay_Therapeutics_Announces_Preclinical_Data_244.pdf.

Cymabay, "CymaBay Therapeutics Announces U.S. Orphan Drug Designation for MBX-8025 in Homozygous Familial Hypercholesterolemia", Mar. 25, 2015, URL: http://content.equisolve.net/cymabay/news/2015-03-25_CymaBay_Therapeutics_Announces_U_S_Orphan_Drug_324.pdf.

(Continued)

*Primary Examiner* — Heidi Reese

(74) *Attorney, Agent, or Firm* — Hamilton Desanctis & Cha, LLP; Sam L. Nguyen

(57) ABSTRACT

Treatment of NAFLD and NASH by therapy with MBX-8025 or an MBX-8025 salt.

13 Claims, No Drawings

(56) References Cited

OTHER PUBLICATIONS

Cymabay, "CymaBay Therapeutics Announces U.S. Orphan Drug Designation for MBX-8025 in Severe Hypertriglyceridemia", Apr. 22, 2015, URL: http://content.equisolve.net/cymabay/news/2015-04-22_CymaBay_Therapeutics_Announces_U_S_Orphan_Drug_336.pdf.
Cymabay, "CymaBay Therapeutics Announces the Initiation of a Phase 2 Study of MBX-8025 in Patients With Homozygous Familial Hypercholesterolemia", Apr. 23, 2015, URL: http://content.equisolve.net/cymabay/news/2015-04-23_CymaBay_Therapeutics_Announces_the_Initiation_of_337.pdf.
Cymabay, "CymaBay Therapeutics Announces the Initiation of a Phase 2 Study of MBX-8025 in Patients With Primary Biliary Cholangitis/Cirrhosis", Nov. 10, 2015, URL: http://content.equisolve.net/cymabay/news/2015-11-10_CymaBay_Therapeutics_Announces_the_Initiation_of_354.pdf.
Cymabay, "CymaBay Therapeutics Announces Positive Results from its Pilot Phase 2 Clinical Study of MBX-8025 in Patients with Homozygous Familial Hypercholesterolemia", Mar. 17, 2016, URL: http://content.equisolve.net/cymabay/news/2016-03-17_CymaBay_Therapeutics_Announces_Positive_Results_361.pdf.
Cymabay, "CymaBay Therapeutics Announces Top Line Efficacy and Safety Data from its Phase 2 Study of MBX-8025 in Patients with Primary Biliary Cholangitis (PBC)", May 31, 2016, URL: http://content.equisolve.net/cymabay/news/2016-05-31_CymaBay_Therapeutics_Announces_Top_Line_Efficacy_370.pdf.
Ewald et al., "Treatment options for severe hypertriglyceridemia (SHTG): the role of apheresis", Clin. Res. Cardiol. Suppl., 7, 31-35 (2012).
FDA, "FDA approves new orphan drug for rare cholesterol disorder", Dec. 26, 2012, URL: http://www.fda.gov/NewsEvents/Newsroom/PressAnnouncements/ucm333285.htm.
FDA, "FDA approves new orphan drug Kynamro to treat inherited cholesterol disorder", Jan. 29, 2013, URL: http://www.fda.gov/NewsEvents/Newsroom/PressAnnouncements/ucm337195.htm.
FDA, "FDA approves Ocaliva for rare, chronic liver disease", May 31, 2016, URL: http://www.fda.gov/NewsEvents/Newsroom/PressAnnouncements/ucm503964.htm.
Firstword Pharma, "Metabolex announces positive results from Phase 2 clinical trial of MBX-8025", Nov. 18, 2008, URL: http://www.firstwordpharma.com/node/35583?tsid=17.
Goldstein et al., "The LDL Receptor", Arterioscler. Thromb. Vasc. Biol., 29, 431-438 (2009).
Gotoda et al., Diagnosis and Management of Type I and Type V Hyperlipoproteinemia, J. Atheroscler. Thromb., 19, 1-12 (2012).
Hata et al., "JTT-130, a Novel Intestine-Specific Inhibitor of Microsomal Triglyceride Transfer Protein, Suppresses Food Intake and Gastric Emptying with the Elevation of Plasma Peptide YY and Glucagon-Like Peptide-1 in a Dietary Fat-Dependent Manner", J. Pharmacol. Exp. Ther., 336, 850-856 (2011).
Haukeland et al., "Abnormal glucose tolerance is a predictor of nonalcoholic steatohepatitis and fibrosis in patients with non-alcoholic fatty liver disease", Scand J. Gastroenterol., 40, 1469-1477 (2005).
Iwaisako et al., "Protection from liver fibrosis by a peroxisome proliferator-activated receptor δ agonist", Proc. Nat. Acad. Sci., 109(2), E1369-E1376 (2012).
Kim et al., "A Small-Molecule Inhibitor of Enterocytic Microsomal Triglyceride Transfer Protein, SLx-4090: Biochemical, Pharmacodynamic, Pharmacokinetic, and Safety Profile", J. Pharmacol. Exp. Ther., 337, 775-785 (2011).
Lindor et al., "AASLD Guidelines: Primary Biliary Cirrhosis", Hepatology, 50, 291-308 (2009).
Lu et al., "Research on the protection effect of PPARδ agonist for non-alcoholic fatty liver disease", J. Gastroenterol. Hepatol., 28 (Suppl. 3), 629 (2013), poster abstract P1601.
Manolis et al., "Novel Hypolipidemic Agents: Focus on PCSK9 Inhibitors", Hosp. Chron., 9(1), 3-10 (2014).
Mera et al., "JTT-130, a Novel Intestine-Specific Inhibitor of Microsomal Triglyceride Transfer Protein, Reduces Food Preference for Fat", J. Diabetes Res., Article 83752 (2014).
Mofrad et al., "Clinical and histological spectrum of nonalcoholic fatty liver disease associated with normal ALT levels", Hepatology, 37, 1286-1292 (2003).
Moorjani et al., "Mutations of low-density-lipoprotein-receptor gene, variation in plasma cholesterol, and expression of coronary heart disease in homozygous familial hypercholesterolemia", Lancet, 341(8856), 1303-1306 (1993).
NCEP, "Third Report of the National Cholesterol Education Program (NCEP) Expert Panel on Detection, Evaluation, and Treatment of High Blood Cholesterol in Adults (Adult Treatment Panel III) Final Report", Circulation, 106, 3143-3422 (2002), URL: http://circ.ahajournals.org/content/106/25/3143.citation; pp. 3143 and 3169 (containing Table II.3—1. Classification of Serum Triglycerides) provided.
NIH, "Omega-3 Fatty Acids and Health: Fact Sheet for Health Professionals"; URL: http://ods.od.nih.gov/factsheets/Omega3FattyAcidsandHealth-HealthProfessional/.
Pang et al., "Critical review of non-statin treatments for dyslipoproteinemia", Expert Rev. Cardiovasc. Ther., 12(3), 359-371 (2014).
Patient.Info, "Primary Biliary Cirrhosis", URL: http://patient.info/doctor/primary-biliary-cirrhosis-pro; accessed Feb. 17, 2016.
Pejic et al. "Hypertriglyceridemia", J. Am. Bd. Fam. Med., 19, 310-316 (2006).
Raal et al., "Homozygous familial hypercholesterolemia: Current perspectives on diagnosis and treatment", Atherosclerosis, 223, 262-268 (2012).
Raal et al., "PCSK9 inhibition with evolocumab (AMG 145) in heterozygous familial hypercholesterolaemia (Rutherford-2): a randomised, double-blind, placebo-controlled trial", Lancet, 385, 9965, 331-340, Jan. 24, 2015; first published online Oct. 1, 2014.
Sahebkar et al., "New peroxisome proliferated receptor agonists: potential treatments for atherogenic dyslipidemia and non-alcoholic fatty liver disease", Expert Opin. Pharmacother., 15(4), 493-503 (2014).
Vroon et al., "Alkaline Phosphatase and Gamma Glutamyltransferase", article at pp. 494-496 of Walker et al., ed., "Clinical Methods: The History, Physical, and Laboratory Examinations", 3rd ed., Butterworths (Boston), 1990. ISBN-10: 0-409-90077-X.
Wikipedia, "Cholestasis", Jun. 11, 2013, URL: http://en.wikipedia.org/w/index.php?title=Cholestasis&oldid=559348356.
Winters, "Low-density lipoprotein apheresis: principles and indications", Sem. Dialysis, 25(2), 145-151 (2012).
Yuan et al., "Hypertriglyceridemia: its etiology, effects and treatment", Can. Med. Assoc. J., 176(8), 1113-1120 (2007).
U.S. Appl. No. 14/541,835, filed Nov. 14, 2014; "Treatment of homozygous familial hypercholesterolemia".
U.S. Appl. No. 14/663,027, filed Mar. 19, 2015; "Treatment of intrahepatic cholestatic diseases".
U.S. Appl. No. 14/749,934, filed Jun. 25, 2015, "Treatment of severe hypertriglyceridemia".
U.S. Appl. No. 15/159,531, filed May 19, 2016; "Treatment of severe hyperlipidemia".
World Health Organization, "Recommended INN: List 77", WHO Drug Information, vol. 31(1), pp. 128-129 (2017).

TREATMENT OF NAFLD AND NASH

CROSS-REFERENCE TO RELATED APPLICATION

This application is a continuation of U.S. application Ser. No. 15/171,910, filed Jun. 2, 2016, now U.S. Pat. No. 9,616,039; which is a continuation of U.S. application Ser. No. 14/684,100, filed Apr. 10, 2015, now U.S. Pat. No. 9,383,181. U.S. application Ser. No. 14/684,100 claims the priority under 35 USC 119(e) of U.S. Application No. 61/978,335, filed Apr. 11, 2014, entitled "Treatment of NAFLD and NASH", which is incorporated into U.S. application Ser. No. 14/684,100 by reference.

BACKGROUND OF THE INVENTION

Field of the Invention

This invention relates to the treatment of non-alcoholic fatty liver disease (NAFLD) and non-alcoholic steatohepatitis (NASH).

Description of the Related Art

NAFLD and NASH

Non-alcoholic fatty liver disease (NAFLD) is a disorder affecting as many as 1 in 3-5 adults and 1 in 10 children in the United States, and refers to conditions where there is an accumulation of excess fat in the liver of people who drink little or no alcohol. The most common form of NAFLD is a non-serious condition called hepatic steatosis (fatty liver), in which fat accumulates in the liver cells: although this is not normal, by itself it probably does not damage the liver. NAFLD most often presents itself in individuals with a constellation of risk factors called the metabolic syndrome, which is characterized by elevated fasting plasma glucose (FPG) with or without intolerance to post-prandial glucose, being overweight or obese, high blood lipids such as cholesterol and triglycerides (TGs) and low high-density lipoprotein cholesterol (HDL-C) levels, and high blood pressure; but not all patients have all the manifestations of the metabolic syndrome. Obesity is thought to be the most common cause of NAFLD; and some experts estimate that about two-thirds of obese adults and one-half of obese children may have fatty liver. The majority of individuals with NAFLD have no symptoms and a normal physical examination (although the liver may be slightly enlarged); children may exhibit symptoms such as abdominal pain and fatigue, and may show patchy dark skin discoloration (acanthosis nigricans). The diagnosis of NAFLD is usually first suspected in an overweight or obese person who is found to have mild elevations in their liver blood tests during routine testing, though NAFLD can be present with normal liver blood tests, or incidentally detected on imaging investigations such as abdominal ultrasound or CT scan. It is confirmed by imaging studies, most commonly a liver ultrasound or magnetic resonance imaging (MRI), and exclusion of other causes.

Some people with NAFLD may develop a more serious condition called non-alcoholic steatohepatitis (NASH): about 2-5% of adult Americans and up to 20% of those who are obese may suffer from NASH. In NASH, fat accumulation in the liver is associated with inflammation and different degrees of scarring. NASH is a potentially serious condition that carries a substantial risk of progression to end-stage liver disease, cirrhosis and hepatocellular carcinoma. Some patients who develop cirrhosis are at risk of liver failure and may eventually require a liver transplant.

NAFLD may be differentiated from NASH by the NAFLD Activity Score (NAS), the sum of the histopathology scores of a liver biopsy for steatosis (0 to 3), lobular inflammation (0 to 2), and hepatocellular ballooning (0 to 2). A NAS of <3 corresponds to NAFLD, 3-4 corresponds to borderline NASH, and ≥5 corresponds to NASH. The biopsy is also scored for fibrosis (0 to 4).

NASH is a leading cause of end-stage liver disease; while NAFLD, and to an even greater degree NASH, are intimately related to states of the metabolic syndrome, including insulin resistance (pre-diabetes) and type 2 diabetes mellitus (T2DM), and abdominal obesity. T2DM has been the most prominent predictor for a poor prognosis in NAFLD, whereas elevated liver enzymes are considered unreliable. NASH develops much more frequently in the presence of longstanding T2DM, and the majority of patients with cryptogenic cirrhosis are obese and/or diabetic. Studies have demonstrated that 60% of patients with T2DM and NAFLD had biopsy-proven NASH, and that advanced hepatic fibrosis was present in 75% of those with diabetes and hypertension compared to only 7% without either condition. Haukeland, "Abnormal glucose tolerance is a predictor of nonalcoholic steatohepatitis and fibrosis in patients with non-alcoholic fatty liver disease", *Scand J. Gastroenterol.*, 40, 1469-1477 (2005), reported that impaired glucose tolerance (IGT) and T2DM were the only independent risk factors for severe NAFLD and NASH, increasing the odds ratio almost 4-fold. Mofrad, "Clinical and histological spectrum of nonalcoholic fatty liver disease associated with normal ALT levels", *Hepatology*, 37, 1286-1292 (2003), reported a study that demonstrated the lack of predictive value for elevated liver transaminases to diagnose NASH in patients with NAFLD and found T2DM to be the only factor independently associated with an increased risk of advanced fibrosis. Thus, NASH is an overlooked complication of T2DM that is frequently associated with fibrosis and in approximately 10% of patients results in cirrhosis; while the risk of hepatocellular carcinoma is also increased in patients with T2DM and NASH. Patients with NAFLD and NASH usually demonstrate mixed dyslipidemia and the other metabolic derangements described above, including an atherogenic low-density lipoprotein (LDL) phenotype consisting of predominantly of small dense particles. Both metabolic syndrome and NAFLD/NASH are characterized by increased cardiovascular inflammation as measured by elevations in high sensitivity C-reactive protein (hsCRP) and other inflammatory cytokines.

There is significant worldwide incidence of obesity, metabolic syndrome, pre-diabetes and diabetes, with the prevalence of diabetes worldwide predicted to double to 366 million by 2030. The US population with diabetes has been estimated at 25.4 million (11.5% prevalence) in 2011 and 37.7 million (14.5%) by 2031, with 20.2% of Hispanic adults having diabetes. Because approximately 70% of persons with T2DM have a fatty liver, and the disease follows a more aggressive course with necroinflammation and fibrosis (i.e., NASH) in diabetes, the epidemiology of diabetes suggests significant increases in NASH and chronic liver disease. Using MRI for the noninvasive assessment of hepatic steatosis, the prevalence of NAFLD, when defined as liver fat >5%, has been estimated to be 34% in the USA or approximately 80 million people, and as many as two out of three obese subjects. However, this prevalence is believed to be much higher in T2DM. In a series of 107 unselected patients with T2DM, the prevalence of NAFLD by MRI was 76%, which is similar to recent studies from Italy and Brazil. Recent studies have indicated that the prevalence of NAFLD is rapidly rising in obese children and adolescents, especially those of Hispanic ancestry.

Treatments for NAFLD and NASH

There are no drugs currently approved to prevent or treat NAFLD or NASH. A number of pharmacological interventions have been tried in NAFLD/NASH but with overall limited benefit. Antioxidant agents may arrest lipid peroxidation and cytoprotective agents stabilize phospholipid membranes, but agents tried unsuccessfully or with only modest benefit so far include ursodeoxycholic acid, vitamins E (α-tocopherol) and C, and pentoxifylline, among others. Weight-loss agents such as orlistat have had no significant benefit compared to just the use of diet and exercise to achieve weight loss ("weight loss alone"). Most weight-loss studies in NAFLD/NASH have been pilot studies of short duration and limited success, reporting only a modest improvement in necroinflammation or fibrosis. A randomized, double-blind, placebo-controlled 6-month trial (Belfort, "A placebo-controlled trial of pioglitazone in subjects with nonalcoholic steatohepatitis", *N. Engl. J. Med.*, 355, 2297-2307 (2006)) of weight loss alone against pioglitazone, a thiazolidinedione peroxisome proliferator-activated receptor-γ (PPARγ) agonist and insulin sensitizer, failed to demonstrate any improvement for weight loss alone, but treatment with pioglitazone improved glycemic control, insulin sensitivity, indicators of systemic inflammation (including hsCRP, tumor necrosis factor-α, and transforming growth factor-β), and liver histology in patients with NASH and IGT or T2DM. Treatment with pioglitazone also ameliorated adipose, hepatic, and muscle IR, and was associated with an approximately 50% decrease in necroinflammation (p<0.002) and a 37% reduction in fibrosis (p=0.08). Improvement in hepatocellular injury and fibrosis has been recently reported in another controlled trial with pioglitazone of 12 months duration. In contrast, while the first randomized clinical study with rosiglitazone, the other thiazolidinedione approved for diabetes treatment, in NASH demonstrated a reduction in IR, plasma alanine aminotransferase (ALT) levels and steatosis, rosiglitazone treatment had no significant effect on necrosis, inflammation, or fibrosis. A preliminary report of the 2-year, open-label follow-up of this trial was also disappointing, with no significant benefit from rosiglitazone treatment. Thus, the pharmacological agent with the most robust efficacy in NASH is pioglitazone. Unfortunately, pioglitazone is also associated with a significantly increased risk of weight gain, edema, congestive heart failure, and osteoporotic fractures in both women and men.

GW510516, a potent peroxisome proliferator-activated receptor-δ (PPARδ) agonist, ameliorated diet-induced obesity and insulin resistance in normal mice, an effect accompanied by enhanced metabolic rate and fatty acid β-oxidation. It also markedly improved diabetes as evidenced by substantial reductions in both glucose and insulin levels in genetically obese ob/ob mice. GW510516 has been shown in two Phase 1 studies in healthy subjects to reduce TGs, low-density-lipoprotein cholesterol (LDL-C), apolipoprotein B (apoB), and insulin levels, and improve HDL-C and insulin sensitivity, with one of the studies also showing a 20% reduction in hepatic fat; while a later study confirmed these effects in dyslipidemic subjects with abdominal obesity (reduction in hepatic fat by 20%, 30% decrease in fasting TGs, 26% reduction in apoB, 23% reduction in LDL-C, 40% reduction in fasting non-esterified fatty acids, and 11% decrease in fasting insulin). However, development of GW510516 was discontinued after observations in animal studies of its association with the rapid development of cancers in several organs.

The dual peroxisome proliferator-activated receptor-α/peroxisome proliferator-activated receptor-δ (PPARα/δ) agonist GFT505 has preferential α ($EC_{50}$=6 nM) and secondary δ ($EC_{50}$=47 nM) agonist activity. The lipid-modifying efficacy of GFT505 has been confirmed in both healthy subjects, as well as in patients with T2DM, combined abdominal obesity and mixed dyslipidemia, combined abdominal obesity and pre-diabetes, atherogenic dyslipidemia, and insulin resistance. These effects include reduction in TGs, non-HDL-C, and total cholesterol, LDL-C, and apoB; and increases in HDL-C. Preclinical studies in rodent models of NAFLD/NASH demonstrated that GFT505 treatment decreased hepatic steatosis, inflammation, and fibrosis, and decreased liver dysfunction markers; while in clinical studies GFT505 has been reported to decrease a range of liver dysfunction markers including ALT, alkaline phosphatase (ALP), and γ-glutamyl transferase (GGT). A 1-year liver biopsy-based Phase2b trial in NASH initially recruited patients for treatment with 80 mg/day of GFT505 or placebo, with an interim safety analysis at 6 months showing no safety issue that compromised the ongoing study; and a second recruitment phase has selected patients for treatment with 120 mg/day of GFT505 or placebo.

Obeticholic acid (OCA, 6α-ethylchenodeoxycholic acid), a semi-synthetic bile acid analog that is a highly potent farnesoid X receptor agonist, was studied in a Phase 2 study for NASH, the FLINT study, sponsored by the US National Institute of Diabetes and Digestive and Kidney Diseases. That study was halted early in January 2014, after about half of the 283 subjects had completed the study, when a planned interim analysis showed that the primary endpoint had been met. The treatment (OCA 25 mg/day for 72 weeks) resulted in a highly statistically significant improvement (p=0.0024 on an intention-to-treat basis, compared to placebo) in the primary histological endpoint, defined as a decrease in NAS of at least two points with no worsening of fibrosis.

Notwithstanding the initial benefits reported for GFT505 and OCA, there still remains a significant unmet clinical need for an effective and well-tolerated drug that can prevent or slow down the progression of NAFLD and NASH.

MBX-8025

MBX-8025 is the compound of the formula

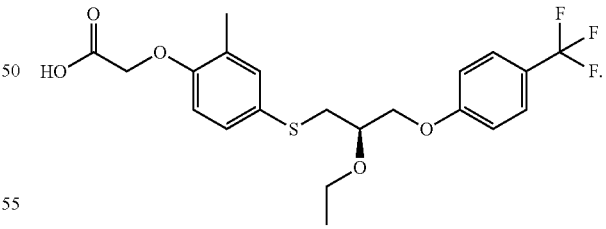

MBX-8025 has the chemical name (R)-2-(4-((2-ethoxy-3-(4-(trifluoromethyl)phenoxy)propyl)-thio)-2-methylphenoxy)acetic acid [IUPAC name as generated by CHEMDRAW ULTRA 12.0]. MBX-8025 and its synthesis, formulation, and use is disclosed in, for example, U.S. Pat. No. 7,301,050 (compound 15 in Table 1, Example M, claim 49), U.S. Pat. No. 7,635,718 (compound 15 in Table 1, Example M), and U.S. Pat. No. 8,106,095 (compound 15 in Table 1, Example M, claim 14). Lysine (L-lysine) salts of MBX-8025 and related compounds are disclosed in U.S.

Pat. No. 7,709,682 (MBX-8025 L-lysine salt throughout the Examples, crystalline forms claimed). MBX-8025 has the International Nonproprietary Name seladelpar ["Recommended INN: List 77", *WHO Drug Information*, vol. 31(1), pp. 128-129 (2017)].

MBX-8025 is an orally active, potent (2 nM) agonist of PPARδ, It is specific (>600-fold and >2500-fold compared with PPARα and PPARγ receptors). PPARδ activation stimulates fatty acid oxidation and utilization, improves plasma lipid and lipoprotein metabolism, glucose utilization, and mitochondrial respiration, and preserves stem cell homeostasis. According to U.S. Pat. No. 7,301,050, PPARδ agonists, such as MBX-8025, are suggested to treat PPARδ-mediated conditions, including "diabetes, cardiovascular diseases, Metabolic X syndrome, hypercholesterolemia, hypo-HDL-cholesterolemia, hyper-LDL-cholesterolemia, dyslipidemia, atherosclerosis, and obesity", with dyslipidemia said to include hypertriglyceridemia and mixed hyperlipidemia.

A Phase 2 study of MBX-8025 L-lysine dihydrate salt in mixed dyslipidemia (6 groups, 30 subjects/group: once daily placebo, atorvastatin (ATV) 20 mg, or MBX-8025 L-lysine dihydrate salt at 50 or 100 mg (calculated as the free acid) capsules alone or combined with ATV 20 mg, for 8 weeks) has been reported by Bays et al., "MBX-8025, A Novel Peroxisome Proliferator Receptor-δ Agonist: Lipid and Other Metabolic Effects in Dyslipidemic Overweight Patients Treated with and without Atorvastatin", *J. Clin. Endocrin. Metab.*, 96(9), 2889-2897 (2011) and Choi et al., "Effects of the PPAR-δ agonist MBX-8025 on atherogenic dyslipidemia", *Atherosclerosis*, 220, 470-476 (2012). Compared to placebo, MBX-8025 alone and in combination with atorvastatin significantly (P<0.05) reduced apoB100 by 20-38%, LDL by 18-43%, triglycerides by 26-30%, non-HDL-C by 18-41%, free fatty acids by 16-28%, and high-sensitivity C-reactive protein by 43-72%; it raised HDL-C by 1-12% and also reduced the number of patients with the metabolic syndrome and a preponderance of small LDL particles. While MBX-8025 at 100 mg/day reduced LDL-C by 22% over the total population treated, the percentage reduction in LDL-C increased to 35% in the tertile with the highest starting LDL-C levels (187-205 mg/dL), and trend analysis on individual patient data confirmed a positive correlation between percentage reduction in LDL-C and starting LDL-C level. MBX-8025 reduced LDL-S/VS by 40-48% compared with a 25% decrease with atorvastatin; and MBX-8025 increased LDL-L by 34-44% compared with a 30% decrease with atorvastatin. MBX-8025 significantly reduced alkaline phosphatase by 32-43%, compared to reductions of only 4% in the control group and 6% in the ATV group; and significantly reduced γ-glutamyl transpeptidase by 24-28%, compared to a reduction of only 3% in the control group and an increase of 2% in the ATV group. Thus MBX-8025 corrects all three lipid abnormalities in mixed dyslipidemia: lowers TGs and LDL and raises HDL, selectively depletes small dense LDL particles (92%), reduces cardiovascular inflammation, and improves other metabolic parameters: increases insulin sensitivity (lowers HOMA-IR, fasting plasma glucose, and insulin), lowers γ-glutamyl transpeptidase and alkaline phosphatase, significantly (>2-fold) reduces the percentage of subjects meeting the criteria for metabolic syndrome, and trends towards a decrease in waist circumference and increase in lean body mass. As explained in US Patent Application Publication No. 2010-0152295, MBX-8025 converts LDL particle size pattern I to pattern A; and from pattern B to pattern I or A, where LDL particle size pattern B is a predominant LDL particle size of less than 25.75 nm, pattern I is a predominant LDL particle size of from 25.75 nm to 26.34 nm, and pattern A is a predominant LDL particle size of greater than 26.34 nm, where the LDL particle size is measured by gradient-gel electrophoresis.

The disclosures of the documents referred to in this application are incorporated into this application by reference.

SUMMARY OF THE INVENTION

This invention is a method of treatment of NAFLD and NASH, comprising administration of MBX-8025 or an MBX-8025 salt.

Because MBX-8025 effectively enhances fatty acid β-oxidation and lowers serum apoB, LDL-C, TGs, non-esterified fatty acids, and hsCRP in clinical and in non-clinical studies, while raising HDL-C in humans, its use will be effective in the treatment of NAFLD and NASH. Further, unlike fenofibrate, MBX-8025 will significantly decrease hepatic fat (assessed by MRI), reduce transaminases, multiple inflammatory cytokines, the hepatocellular apoptosis marker CK18, improve the LDL phenotype, and demonstrate improvement in multiple glycemic parameters including glycated hemoglobin (HbA1c), FPG, fasting insulin, and HOMA-IR. Because the presence of >6% hepatic fat content by MRI in obese subjects with insulin resistance is very predictive of both NAFLD and NASH, reduction of hepatic fat by treatment with MBX-8025 will be significant in the treatment of NAFLD and NASH.

Preferred embodiments of this invention are characterized by the specification and by the features of Claims 1 to 14 of this application as filed.

DETAILED DESCRIPTION OF THE INVENTION

Definitions

"NAFLD and NASH" and their treatment are described in paragraphs [0003] through [0013] the Description of the Related Art, under "NAFLD and NASH" and "Treatments for NAFLD and NASH".

A "therapeutically effective amount" of MBX-8025 or an MBX-8025 salt means that amount which, when administered to a human for treating NAFLD or NASH, is sufficient to effect treatment for the NAFLD or NASH. "Treating" or "treatment" of NAFLD or NASH in a human includes one or more of:

(1) preventing or reducing the risk of developing NAFLD or NASH, i.e., causing the clinical symptoms of NAFLD or NASH not to develop in a subject who may be predisposed to NAFLD or NASH but who does not yet experience or display symptoms of the NAFLD or NASH (i.e. prophylaxis);

(2) inhibiting NAFLD or NASH, i.e., arresting or reducing the development of NAFLD or NASH or its clinical symptoms; and (3) relieving NAFLD or NASH, i.e., causing regression, reversal, or amelioration of the NAFLD or NASH or reducing the number, frequency, duration or severity of its clinical symptoms. The therapeutically effective amount for a particular subject varies depending upon the health and physical condition of the subject to be treated, the extent of the NAFLD or NASH, the assessment of the medical situation, and other relevant factors. It is expected that the therapeutically effective amount will fall in a relatively broad range that can be determined through routine trial.

"MBX-8025" is described in paragraphs [0015] through [0018] the Description of the Related Art, under "MBX-8025".

Salts (for example, pharmaceutically acceptable salts) of MBX-8025 are included in this invention and are useful in the compositions, methods, and uses described in this application. These salts are preferably formed with pharmaceutically acceptable acids. See, for example, "Handbook of Pharmaceutically Acceptable Salts", Stahl and Wermuth, eds., Verlag Helvetica Chimica Acta, Zürich, Switzerland, for an extensive discussion of pharmaceutical salts, their selection, preparation, and use. Unless the context requires otherwise, reference to MBX-8025 is a reference both to the compound and to its salts.

Because MBX-8025 contains a carboxyl group, it may form salts when the acidic proton present reacts with inorganic or organic bases. Typically the MBX-8025 is treated with an excess of an alkaline reagent, such as hydroxide, carbonate or alkoxide, containing an appropriate cation. Cations such as $Na^+$, $K^+$, $Ca^{2+}$, $Mg^{2+}$, and $NH_4^+$ are examples of cations present in pharmaceutically acceptable salts. Suitable inorganic bases, therefore, include calcium hydroxide, potassium hydroxide, sodium carbonate and sodium hydroxide. Salts may also be prepared using organic bases, such as salts of primary, secondary and tertiary amines, substituted amines including naturally-occurring substituted amines, and cyclic amines, including isopropylamine, trimethylamine, diethylamine, triethylamine, tripropylamine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, N-ethylpiperidine, and the like. As noted in the Description of the Related Art, under "MBX-8025", MBX-8025 is currently formulated as its L-lysine dihydrate salt; and MBX-8025 has also been studied in clinical trials as its calcium salt.

"Comprising" or "containing" and their grammatical variants are words of inclusion and not of limitation and mean to specify the presence of stated components, groups, steps, and the like but not to exclude the presence or addition of other components, groups, steps, and the like. Thus "comprising" does not mean "consisting of", "consisting substantially of", or "consisting only of"; and, for example, a formulation "comprising" a compound must contain that compound but also may contain other active ingredients and/or excipients.

Formulation and Administration

The MBX-8025 may be administered by any route suitable to the subject being treated and the nature of the subject's condition. Routes of administration include administration by injection, including intravenous, intraperitoneal, intramuscular, and subcutaneous injection, by transmucosal or transdermal delivery, through topical applications, nasal spray, suppository and the like or may be administered orally.

Formulations may optionally be liposomal formulations, emulsions, formulations designed to administer the drug across mucosal membranes or transdermal formulations. Suitable formulations for each of these methods of administration may be found, for example, in "Remington: The Science and Practice of Pharmacy", 20th ed., Gennaro, ed., Lippincott Williams & Wilkins, Philadelphia, Pa., U.S.A. Because MBX-8025 is orally available, typical formulations will be oral, and typical dosage forms will be tablets or capsules for oral administration. As mentioned in the Description of the Related Art, under "MBX-8025", MBX-8025 has been formulated in capsules for clinical trials.

Depending on the intended mode of administration, the pharmaceutical compositions may be in the form of solid, semi-solid or liquid dosage forms, preferably in unit dosage form suitable for single administration of a precise dosage. In addition to an effective amount of the MBX-8025, the compositions may contain suitable pharmaceutically-acceptable excipients, including adjuvants which facilitate processing of the active compounds into preparations which can be used pharmaceutically. "Pharmaceutically acceptable excipient" refers to an excipient or mixture of excipients which does not interfere with the effectiveness of the biological activity of the active compound(s) and which is not toxic or otherwise undesirable to the subject to which it is administered.

For solid compositions, conventional excipients include, for example, pharmaceutical grades of mannitol, lactose, starch, magnesium stearate, sodium saccharin, talc, cellulose, glucose, sucrose, magnesium carbonate, and the like. Liquid pharmacologically administrable compositions can, for example, be prepared by dissolving, dispersing, etc., an active compound as described herein and optional pharmaceutical adjuvants in water or an aqueous excipient, such as, for example, water, saline, aqueous dextrose, and the like, to form a solution or suspension. If desired, the pharmaceutical composition to be administered may also contain minor amounts of nontoxic auxiliary excipients such as wetting or emulsifying agents, pH buffering agents and the like, for example, sodium acetate, sorbitan monolaurate, triethanolamine sodium acetate, triethanolamine oleate, etc.

For oral administration, the composition will generally take the form of a tablet or capsule, or it may be an aqueous or nonaqueous solution, suspension or syrup. Tablets and capsules are preferred oral administration forms. Tablets and capsules for oral use will generally include one or more commonly used excipients such as lactose and corn starch. Lubricating agents, such as magnesium stearate, are also typically added. When liquid suspensions are used, the active agent may be combined with emulsifying and suspending excipients.

If desired, flavoring, coloring and/or sweetening agents may be added as well. Other optional excipients for incorporation into an oral formulation include preservatives, suspending agents, thickening agents, and the like.

Typically, a pharmaceutical composition of MBX-8025, or a kit comprising compositions of MBX-8025, is packaged in a container with a label, or instructions, or both, indicating use of the pharmaceutical composition or kit in the treatment of NAFLD and/or NASH.

A suitable amount of MBX-8025 (calculated as the free acid) for oral dosing will be 20-200 mg/day, preferably 50-100 mg/day, for an adult subject with NAFLD or NASH, depending on the disease and stage of disease and factors such as hepatic and renal function. That is, a suitable amount of MBX-8025 for oral dosing will be similar to the amounts employed in clinical trials; though it is possible that the therapeutically effective amount may be higher in severe cases of NAFLD or NASH. Suitable reductions in dose toward the lower end of the outer range above will be made for subjects who are children, depending on such additional factors as age and body mass.

A person of ordinary skill in the art of the treatment of NAFLD or NASH will be able to ascertain a therapeutically effective amount of the MBX-8025 or an MBX-8025 salt for a particular stage of disease to achieve a therapeutically effective amount without undue experimentation and in reliance upon personal knowledge and the disclosure of this application.

Example

Subjects with NAFLD or NASH are treated with doses of either 50 or 100 mg/day of MBX-8025 for 6 months. Subjects are permitted their usual other medications (e.g. antidiabetic medications such as metformin or sulfonamides) but not glitazones, PPAR agonists, OCA, or similar medications. The subjects are assessed before the study, and at intervals during the study, such as every 4 weeks during the study and 4 weeks after the last dose of the MBX-8025 therapy, for safety and pharmacodynamic evaluations.

MRIs of the subjects' livers are taken every 4 weeks during the study and 4 weeks after completion of MBX-8025 dosing, to determine hepatic fat; and liver biopsies are taken before the study (to establish the diagnosis) and 4 weeks after completion of MBX-8025 dosing. At each visit, after a 12-hour fast, blood is drawn and urine collected; and a standard metabolic panel, complete blood count, and standard urinalysis are performed. Blood is analyzed for total cholesterol, HDL-C, LDL-C, VLDL-C, TGs, apoB, and liver transaminases. The subjects also maintain health diaries, which are reviewed at each visit. The subjects show a dose-related improvement in their disease, as manifested by, for example, MRI and liver biopsy.

While this invention has been described in conjunction with specific embodiments and examples, it will be apparent to a person of ordinary skill in the art, having regard to that skill and this disclosure, that equivalents of the specifically disclosed materials and methods will also be applicable to this invention; and such equivalents are intended to be included within the following claims.

What is claimed is:

1. A method for decreasing hepatic fat in a subject having a disease that is non-alcoholic fatty liver disease (NAFLD) or non-alcoholic steatohepatitis (NASH) comprising administering a therapeutically effective amount of seladelpar or a salt thereof to the subject.

2. A method for decreasing hepatic fat in a subject having a disease that is non-alcoholic fatty liver disease (NAFLD) or non-alcoholic steatohepatitis (NASH) comprising orally administering a therapeutically effective amount of seladelpar or a salt thereof to the subject.

3. The method of claim 2 where the daily dose of the seladelpar or a salt thereof administered to the subject is 20-200 mg, when the dose is calculated as seladelpar.

4. The method of claim 3 where the daily dose of the seladelpar or a salt thereof administered to the subject is 50-100 mg, when the dose is calculated as seladelpar.

5. The method of claim 2 where the seladelpar or a salt thereof is administered to the subject once/day.

6. The method of claim 2 where the disease is NAFLD.

7. The method of claim 2 where the disease is NASH.

8. A method for decreasing hepatic fat in a subject having a disease that is non-alcoholic fatty liver disease (NAFLD) or non-alcoholic steatohepatitis (NASH) comprising orally administering a therapeutically effective amount of seladelpar L-lysine dihydrate salt to the subject.

9. The method of claim 8 where the daily dose of the seladelpar L-lysine dihydrate salt administered to the subject is 20-200 mg, when the dose is calculated as seladelpar.

10. The method of claim 9 where the daily dose of the seladelpar L-lysine dihydrate salt administered to the subject is 50-100 mg, when the dose is calculated as seladelpar.

11. The method of claim 8 where the seladelpar L-lysine dihydrate salt is administered to the subject once/day.

12. The method of claim 8 where the disease is NAFLD.

13. The method of claim 8 where the disease is NASH.

* * * * *